United States Patent [19]

Baniel et al.

[11] Patent Number: 5,510,526
[45] Date of Patent: Apr. 23, 1996

[54] LACTIC ACID PRODUCTION, SEPARATION AND/OR RECOVERY PROCESS

[75] Inventors: Abraham M. Baniel; Aharon M. Eyal, both of Jerusalem; Joseph Mizrahi, Haifa; Betty Hazan, Jerusalem, all of Israel; Rod R. Fisher, Eden Prairie, Minn.; Jeffrey J. Kolstad, Wayzata, Minn.; Brenda F. Stewart, White Bear Lake, Minn.

[73] Assignee: Cargill, Incorporated, Wayzata, Minn.

[21] Appl. No.: 207,773

[22] Filed: Mar. 8, 1994

Related U.S. Application Data

[63] Continuation-in-part of Ser. No. 84,810, Jun. 29, 1993, abandoned.

[51] Int. Cl.⁶ .................... C07C 51/48; C07C 51/42
[52] U.S. Cl. ................................. 562/580; 562/589
[58] Field of Search ........................ 562/580, 589

[56] References Cited

U.S. PATENT DOCUMENTS

| | | | |
|---|---|---|---|
| 2,539,472 | 1/1951 | Ratchford et al. | 260/535 |
| 4,275,234 | 6/1981 | Baniel et al. | 562/584 |
| 4,282,323 | 8/1981 | Yates | 435/140 |
| 4,444,881 | 4/1984 | Urbas | 435/139 |
| 4,698,303 | 10/1987 | Bailey et al. | 435/139 |
| 5,132,456 | 7/1992 | King et al. | 562/593 |

OTHER PUBLICATIONS

Proceedings of the International Solvent Extraction Conference, vol. 3, issued 1974, R. Blumberg et al., "Interesting Aspects in the Development of a Novel Solvent Extraction Process for Producing Sodium Bicarbonate", pp. 2789–2802.

*Primary Examiner*—José G. Dees
*Assistant Examiner*—Barbara S. Frazier
*Attorney, Agent, or Firm*—Dorsey & Whitney

[57] ABSTRACT

A process for the production of lactic acid and for the separation and/or recovery of lactic acid from a lactate feed solution. A lactate feed solution preferably obtained from a fermentation broth is combined with and extracted by a water immiscible trialkyl amine in the presence of carbon dioxide. Lactic acid is recovered from the resulting organic phase. Recovered carbonate or bicarbonate from the aqueous phase is preferably recycled to the fermentor and regenerated extractant is preferably recycled for use in the extraction.

30 Claims, 1 Drawing Sheet

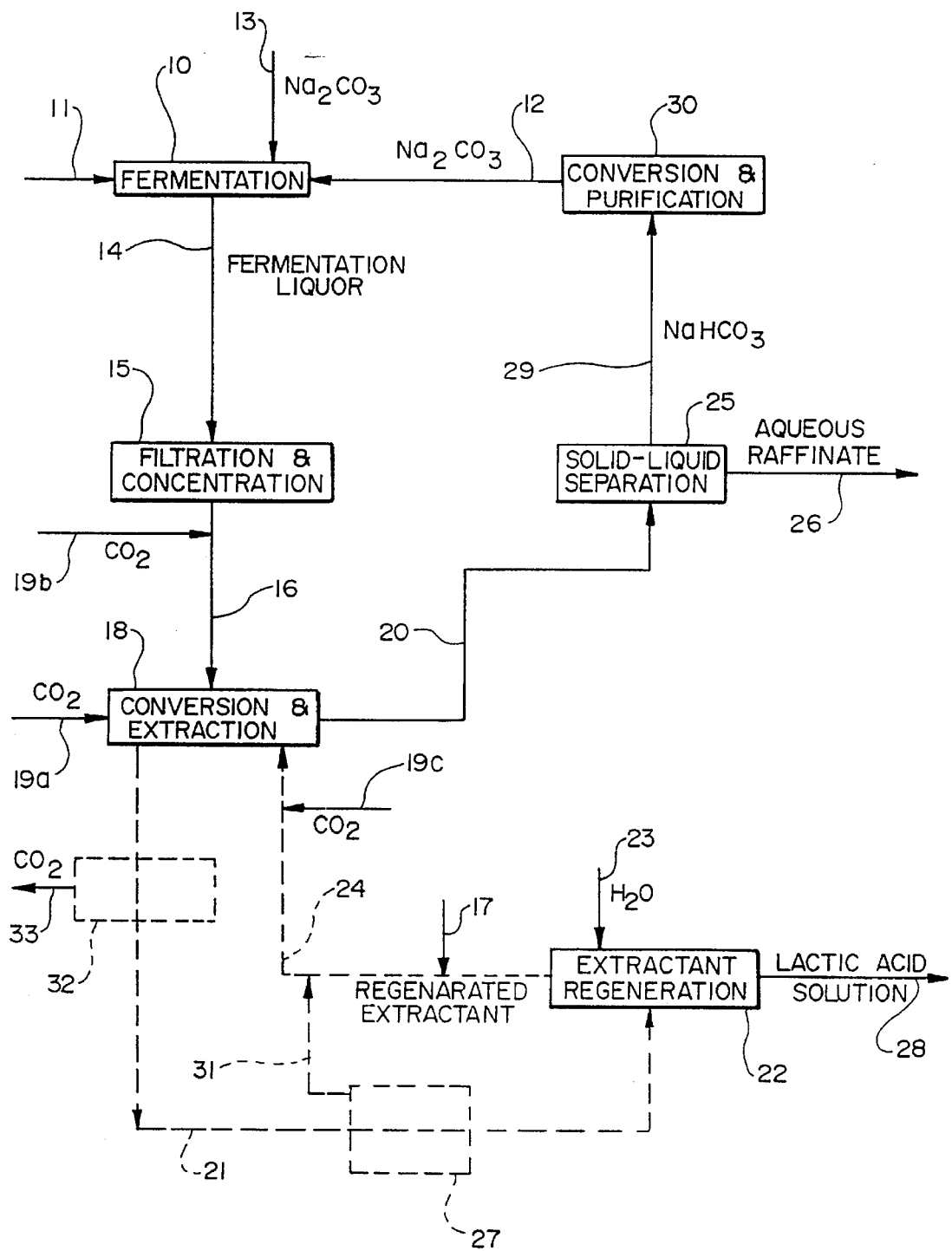

LACTIC ACID PRODUCTION, SEPARATION AND/OR RECOVERY PROCESS

This is a continuation-in-part of Ser. No. 08/084,810, filed Jun. 29, 1993, now abandoned.

BACKGROUND OF THE INVENTION

1. Field of the Invention

The present invention relates generally to the production, separation and/or recovery of lactic acid and more particularly to the production, separation and recovery of lactic acid via a fermentation process and the separation and/or recovery of lactic acid from a lactate feed solution such as is obtained from a fermentation broth or other sources.

2. Description of the Prior Art

Lactic acid has long been used as a food additive and in various chemical and pharmaceutical applications. More recently, lactic acid has been used in the making of biodegradable polymers both as a replacement for present plastic materials as well as various new uses where biodegradability is needed or desired. Accordingly, there is an ever increasing demand for lactic acid. The present invention aims at meeting this demand by providing an efficient and environmentally friendly process for producing lactic acid which avoids the consumption of bases and acids and substantially reduces, if not eliminates, the formation of waste or byproduct salts.

Production of lactic acid is commonly carried out by fermentation of a strain of the bacterial genus Lactobacillus and more particularly by the species *Lactobacillus delbrueckii* or *Lactobacillus acidophilus* as examples. In general, the production of lactic acid by fermentation in a fermentation broth is well known in the art. The fermentation substrate consists of carbohydrates together with suitable mineral and proteinaceous nutrients. Because the lactic acid producing microorganisms are inhibited in a strongly acidic environment, the pH of the fermentation broth must be kept above 4.5, and preferably within the range of about 5.0 to 7.0, more preferably within the range of about 5.5 to 6.5, and most preferably within the range of about 6.0 to 6.5. To maintain this pH level, suitable water-soluble basic substances or agents that are non-toxic to the acid producing microorganism, such as alkali metal hydroxides, carbonates or bicarbonates or alkaline earth metal hydroxides or carbonates, are commonly added to the fermentation broth to neutralize the acid being produced. This results in the formation of a lactate solution rather than the desired lactic acid product. Such lactate solution contains the lactate anion and the corresponding cation of the substance used to neutralize the fermentation broth.

Various methods have been proposed for the recovery of lactic acid from a fermentation broth. Where the fermentation is carried out in the presence of calcium carbonate, it is possible to recover the lactic acid by acidification with sulfuric acid. This results in the precipitation of calcium sulfate, while free lactic acid remains in the mother liquor. If desired, the mother liquor may be concentrated to up to about 90% by weight lactic acid. Subsequently, lactic acid may be extracted from the mother liquor with a suitable organic extractant to yield an extract which is back-extracted with water or the acid may be adsorbed on a suitable adsorbent and later desorbed. The resulting aqueous lactic acid solution may then be concentrated. This method has the disadvantage that it irreversibly consumes calcium carbonate and sulfuric acid and leaves, as waste, large quantities of calcium sulfate which give rise to disposal problems.

U.S. Pat. No. 5,132,456 (King et al.) describes a process for recovering carboxylic acid from a carboxylic acid-containing aqueous feed stream having a pH close to or above the $pK_a$ level of the acid. In accordance with that process the recovery involves what may be described as a cascade type acid withdrawal operation in which the basicity of the extractant is increased stepwise. In a first stage of the process, the feed stream is contacted with an adsorbent such as a strongly basic extractant or a solid anion exchanger. In a second stage the acid-loaded adsorbent is contacted with an aqueous solution of ammonia or a low molecular weight trialkyl amine having a stronger affinity to the carboxylic acid that is being recovered than the adsorber used in the first stage. In this way an aqueous solution of a water-soluble carboxylic acid ammonium salt is formed. This is then subjected to heat treatment, whereby the salt is decomposed to yield back the trialkyl amine or ammonia and free carboxylic acid. Applying this process to lactic acid involves the formation of salts of lactic acid with strong bases having a $pK_a$ value of about 9–11. Thus, the decomposition of these salts into free lactic acid is energy intensive. Examples 12–14 of the patent mention the use of Alamine 336 (tricaprylylamine) for the extraction of, among others, lactic acid from an aqueous solution, but no yields are mentioned. By the extraction of even small quantities of lactic acid from a fermentation broth the pH of the broth rises rapidly to above 7. As shown in FIGS. 3 and 4 of this patent, the uptake of carboxylic acids from aqueous solutions drops rapidly with an increase of the pH. It is, therefore, inherent in these examples that the lactic acid uptake, if any, is negligible. It is further noted that upon heat treatment and concentration of an ammonium lactate, crystalline lactic acid does not precipitate and instead the viscosity of the solutions increases steadily as a result of self-association of the acid. It is thus evident that the process of U.S. Pat. No. 5,132,456 is unsuitable for the recovery of lactic acid from a fermentation broth.

U.S. Pat. Nos. 4,444,881 and 4,405,717 (Urbas) describe a process for the recovery of an organic acid from a diluted aqueous solution of its calcium salt by adding a water-soluble trialkyl amine carbonate to the solution to form on the one hand a water soluble trialkyl ammonium salt of the acid, which salt remains in solution, and on the other hand calcium carbonate which precipitates. After removal of the calcium carbonate the remaining mother liquor is heated for the separate recovery of the amine and the product acid. The water-soluble trialkyl amines employed in accordance with these patents are strongly basic. Accordingly, the decomposition of the trialkylammonium salts into free acids is energy intensive.

U.S. Pat. No. 4,282,323 (Yates) describes a process for obtaining lower carboxylic acids from a salt solution of such carboxylic acid as obtained from fermentation. The process appears to be applicable to a restricted number of lower aliphatic and aromatic monocarboxylic acids and is specifically described only in relation to acetic acid. In accordance with that process, the aqueous solution of a carboxylic acid salt is contacted in the presence of a liquid polar organic solvent serving as extractant, with pressurized carbon dioxide, to convert at least part of the salt to the corresponding free acid which is taken up by the organic phase from where it is subsequently recovered. It is inherent in the use of a polar organic extractant that the bulk of the carboxylic acid remains in the neutral to basic aqueous phase, and indeed the recovery rates reported in U.S. Pat. No. 4,282,323 are low, ranging between 4.8% and 18% of the acid initially present.

U.S. Pat. No. 4,275,234 (Baniel) is directed to a method of recovering various acids in their free form from aqueous solutions. Thus, the process of Baniel is not applicable to a lactate solution of the type commonly obtained from a fermentation process or from other sources. The essence of the Baniel U.S. Pat. No. 4,275,234 is the discovery that efficient back-extraction can be achieved by performing the back-extraction at a temperature higher than that of the primary extraction.

R. Bar and J. L. Geiner, Biotechnology Progress 3, 109 (1987) studied the feasibility of extracting lactic acid from aqueous solution by means of a long-chain trialkyl amine of low basicity, such as tridodecylamine, using various tridodecylamine solutions in n-dodecanol. It was found that extraction of lactic acid by extraction with a long-chain trialkyl amine such as tridodecylamine was effective only at a pH that is lower than the $pK_a$ of lactic acid, the latter of which is 3.86. At such a low pH, however, the lactic acid fermenting microorganism such as, for example, *Lactobacillus delbrueckii* or *Lactobacillus acidophilus* is severely inhibited.

To sum up, the prior art teaches that when using amines for the recovery of lactic acid from a lactate solution such as that obtained from a fermentation broth, either by way of extraction or by way of ammonuim salt formation, only strongly basic water soluble amines can be used, while water immiscible amines of weak basicity, such as long-chain trialkyl amines, are unsuitable. Accordingly, a need exists for a lactic acid production process which is energy efficient, is environmentally friendly, consumes no acids or bases and which minimizes, if not eliminates, generation of waste salts or emissions.

SUMMARY OF THE INVENTION

In accordance with the present invention, and contrary to the teachings of the prior art, it has surprisingly been found that it is possible to separate and recover lactic acid from a lactate solution at a pH in the range of 4 to 14 in a nearly quantitative fashion by a process meeting the above objectives. More specifically, the lactic acid separation and recovery process includes an extraction (hereinafter sometimes referred to as the primary or forward extraction) in the presence of a water immiscible, long-chain trialkyl amine and carbon dioxide. The lactate solution may be obtained from a fermentation broth or from hydrolyzed polylactide via polylactide recycling or recovery, among possible others.

Preferably the invention provides a process for the separation and/or recovery of lactic acid from a lactate solution formed by fermentation in the presence of a basic substance selected from the group of alkali metal, alkaline earth metal or ammonium hydroxides, carbonates or bicarbonates. The process steps comprise obtaining a lactate feed solution from a fermentation broth or another source and combining such feed solution with an extractant comprising a trialkyl amine in the presence of carbon dioxide, where the trialkyl amine is water immiscible and has a total of at least 18 carbon atoms. The term "combining" as used herein is intended to mean a mixing or contacting of the lactate solution and the amine so that extraction can occur. Preferably the lactate feed solution is formed by filtering a fermentation broth to remove biomass and other solids and the combining of the lactate solution and extractant occurs in the presence of carbon dioxide at a partial pressure of at least about 50 psig.

The above extraction in accordance with the present invention results in the formation of a lactic acid rich organic phase and an aqueous or aqueous-slurry phase. Each of these two phases, in accordance with preferred further aspects of the invention, is processed to recover lactic acid from the organic phase and carbonate or bicarbonate from the aqueous phase. Preferably, the recovered carbonate or bicarbonate is recycled to the fermentor. The organic phase from which the lactic acid has been recovered is recycled for use in the primary extraction. This results in a process in which the consumption of acids and bases is avoided and in which the generation of waste salts and other by-products is substantially reduced, if not eliminated.

In a preferred process of the present invention, a countercurrent liquid-liquid extractor or extraction unit is used. During steady state operation, the lactate feed solution and extractant are loaded into the extractor and operated in the presence of pressurized carbon dioxide. The optimum operational pressure or pressure range may be established for each particular case. The particular pressure is not critical provided sufficient carbon dioxide is present for the primary extraction to occur. Preferably the partial pressure of carbon dioxide is maintained at 50 psig or greater. Upon leaving the extractor, the organic phase may be subjected to decompression. This results in a release of the pressurized carbon dioxide which can, if desired, be recovered for reuse in the process.

The long-chain trialkyl amines useful in accordance with the present invention are those in which the amines and the amine lactate salts are immiscible with water and have a total of at least 18 carbon atoms, and preferably from 24 to 42 carbon atoms. Typical examples of such amines are trihexylamine, trioctylamine, triisooctylamine, tricaprylylamine and tridodecylamine. As used herein, the term amine salt or amine lactate salt refers to the species formed when lactic acid is extracted into the amine extractant phase, although the exact nature of this species is not known.

The extraction process of the present invention may be performed batchwise or continuously, but dramatically improved separation and ultimate recovery can be achieved with a continuous process and in particular a countercurrent extraction process.

Solvents of the trialkyl amines of the present process may also be used, if desired, as part of the extractant. These may be used for the purpose of diluting certain relatively viscous trialkyl amines, enhancing the extraction, and/or stabilizing and maintaining the organic phase in a single phase substantially immiscible with water. Any compatible organic solvent capable of dissolving the amine and the amine lactate salt is suitable provided it is also inert to chemical reaction both with the long-chain trialkyl amines utilized and to the amine lactate salt and lactic acid. As used herein, the term "compatible" means miscible with, soluble in and chemically inert. The usefulness of solvents for these purposes is well known in the art. Specific examples, however, include liquid hydrocarbons such as kerosene or mineral oils, alkanols such as isopropanol, n-butanol and n-octanol and various ketones such as methyl-isobutyl ketone (MiBK) and nonanone, among others. If desired, two or more different solvents may be used, e.g. a hydrocarbon and an alkanol.

The organic phase resulting from the primary or forward extraction is subjected to a separation process such as further extraction, vaporization or the like to recover the lactic acid. Preferably, the organic phase is subjected to back-extraction with water to recover the lactic acid in an aqueous phase. Where the initial extracting medium also contains an alkanol or ketone as a solvent, the back-extraction may be preceded by removal of the solvent through azeotropic steam distillation or other techniques. That portion of the organic phase remaining after separation of the lactic acid and, where applicable, the separately recovered alkanol or ketone, may be recycled for use in the primary extraction. The aqueous lactic acid solution resulting from the back-extraction is removed as product and may be concentrated, if desired.

In a preferred embodiment of the process, carbonate or bicarbonate is present in the aqueous phase either in solution or as a solid suspension, predominantly in the form of an alkali metal, alkaline earth metal or ammonium carbonate or bicarbonate, depending on the cation present in the lactate solution. This aqueous phase is preferably a suspension of sodium bicarbonate crystals and is subjected to solid-liquid separation followed by conversion of the bicarbonate into sodium carbonate by heat treatment or other techniques known in the art. Carbon dioxide liberated during this conversion may be trapped and recycled for use in the primary extraction. The solid-liquid separation also yields an aqueous raffinate substantially depleted of lactate which is withdrawn and may be used as a constituent of animal feed.

Accordingly, it is an object of the present invention to provide a process for separating and/or recovering lactic acid from a lactate solution which does not involve consumption of acids and bases and which avoids generation of waste salts.

A further object of the present invention is to provide a process for separating and/or recovering lactic acid from a lactate solution which requires minimal energy use and results in minimal, if any, plant emissions.

A still further object of the present invention is to provide a process for producing lactic acid from a fermentation process which uses environmentally friendly materials and in which substantially all by products of the production process are recycled.

Another object of the present invention is to provide a process for separating and/or recovering lactic acid from a lactate feed solution utilizing a long-chain trialkyl amine in the presence of carbon dioxide.

These and other objects of the present invention will become apparent with reference to the drawing, the description of the preferred embodiment and process, the examples and the appended claims.

DESCRIPTION OF THE DRAWING

The single FIGURE of the drawing is a block diagram representing the preferred embodiment of the process according to the present invention.

DESCRIPTION OF THE PREFERRED EMBODIMENT AND PROCESS

With reference to the drawing, lactic acid fermentation is carried out in a fermentor 10 in which carbohydrates are fermented and converted to lactic acid by the bacterial genus Lactobacillus and more specifically by the microorganism *Lactobacillus acidophilus*. Because many organisms which are attractive in such a fermentation process cannot tolerate acidic conditions with a pH lower than about 3.8, the acids formed by this process must be at least partly neutralized to maintain the pH above such level and more preferably above a pH of 4.5 to allow the fermentation to continue. In accordance with the preferred process, a neutralizing agent such as the alkali metal, alkaline earth metal or ammonium hydroxides, carbonates or bicarbonates are used for this purpose. In the preferred process, sodium carbonate ($Na_2CO_3$) is added to the fermentor 10 for this purpose, either via the recycle 12 as discussed below or along the path 13. Preferably, sufficient sodium carbonate or other alkaline substance is provided to the fermentor 10 to maintain the pH of the fermentation broth at a pH above 5.0 and preferably in the range of about 5.0 to 7.0, more preferably in the range of about 5.5 to 6.5 and most preferably in the range of about 6.0 to 6.5. Other ingredients may also be used in the fermentation process which is well known in the art.

In the fermentor 10, the carbohydrate is converted to lactic acid which immediately is converted to a lactate form in the presence of the neutralizing agent. In the preferred process using sodium carbonate, sodium lactate [$NaCH_3CH(OH)COO$] is formed. A portion of the fermentation broth or liquor is continuously or intermittently withdrawn from the fermentor 10 via the path 14 and exposed to a filtration and concentration unit 15. The unit 15 functions to physically remove, via filtration or ultrafiltration, biomass and other solids which can be recycled to the fermentor 10, if desired. The filtrate comprises an aqueous lactate solution which contains the lactate salt comprised of the lactate anion together with the cation of the neutralizing agent. In the preferred process, the filtrate is comprised principally of sodium lactate. This solution, which commonly comprises between about 0.25% and 50% by weight of sodium lactate, may be concentrated by water evaporation or other techniques to improve the overall lactic acid production efficiency. In the preferred process, the filtered lactate solution is concentrated by water evaporation to about 40% to 70% by weight sodium lactate; however, such concentration is optional.

The sodium lactate solution exiting from the filtration and concentration unit 15 comprises a lactate feed solution which is fed into an extraction unit 18 along the path 16. The unit 18 is part of an extraction system which also includes the extractant regeneration unit 22, the organic phase stream 21 and the extractant recycle stream 24. Within the unit 18, the lactate feed solution is combined with an extractant comprised of at least one water immiscible trialkyl amine in the presence of carbon dioxide, where the amine has a total of at least 18 carbon atoms. Within the unit 18, two separate phases are formed: an organic phase containing the extractant and extracted lactic acid and an aqueous or aqueous-slurry phase containing the carbonate or bicarbonate salt of the cation of the neutralizing agent. In the preferred process, the aqueous phase contains sodium carbonate or bicarbonate. The unit 18 may comprise any one of a variety of single or multi-stage pressure extraction units. In the preferred process, the unit 18 is a multi-stage countercurrent extraction unit.

In the preferred process, the extraction system is initially charged with the trialkyl amine. The amine may be introduced by directly adding it to the unit 18 or by adding it to the recycle stream 24 through the amine make-up stream 17. During steady state operation, little if any additional trialkyl amine will be needed. To the extent it is, however, it can be added to the recycle stream 24 via the make-up stream 17.

Carbon dioxide may be added directly to the unit 18 under pressure via the path 19a, to the organic recycle stream 24 under pressure via the path 19c, or to the aqueous lactate stream 16 under pressure via the path 19b. In the preferred process as illustrated, the organic recycle stream 24 is preloaded with carbon dioxide by adding carbon dioxide under pressure via the stream 19c prior to the unit 18. In any case, the carbon dioxide within the unit 18 should preferably be maintained at a partial pressure of at least about 50 psig, more preferably at a partial pressure of at least 75 psig and most preferably between about 150–300 psig.

Although it is believed that some extraction of lactic acid from a lactate solution is possible with any water immiscible trialkyl amine in the presence of carbon dioxide, the particular degree of extraction will vary with the amine utilized and the carbon dioxide pressure. The degree of extraction can also be enhanced or otherwise affected by various solvents as described below and as known in the art. The degree of extraction will generally be dependent on the partition coefficient and the number of stages used in the extraction process. As used herein, the partition coefficient is the mass concentration of lactic anion in the organic phase divided by the mass concentration of lactate expressed as lactic acid equivalent in the aqueous phase. Usually, for a particular system, the partition coefficient, within limits, will vary directly with the carbon dioxide pressure. As the partition coefficient increases, the number of stages needed to achieve a particular degree of extraction will decrease. Carbon dioxide and amine composition should preferably be sufficiently high to avoid excessive extractant phase necessary to extract the acid.

The trialkyl amines which are useful in the process of the present invention are those which are water immiscible and relatively weak. Specifically, these are the trialkyl amines having a total of at least 18 carbon atoms and preferably about 24 to 42 carbon atoms. The practical lower limit of the number of carbon atoms is limited by the increasing water solubility of the smaller trialkyl amines or their salts. The water immiscibility of the trialkyl amines with 18 or more carbon atoms is well known in the art. The practical upper limit of the number of amine carbon atoms is determined by the molar concentration of amine obtainable in the organic phase. Specifically, the extraction ability of the trialkyl amines is dependent on the molar concentration of the amine component. Thus, as the molecular weight of the amine increases, the molar concentration of the amine component (or a pure amine solution) will decrease. The trialkyl amine should also be sufficiently strong to extract the lactic acid from the aqueous lactate feed, but sufficiently weak to enable water to back extract the lactic acid from the organic phase. Typical examples of such amines which meet the above requirements, are readily available and are useful in the process of the present invention are one or more of trihexylamine, trioctylamine, triisooctylamine, tricaprylylamine, tridodecylamine and mixtures thereof.

The particular ratios of lactate feed solution and trialkyl amine phase which are fed to the unit 18 along the paths 16 and 24, respectively, will depend on a variety of factors including the concentration of the sodium lactate and the concentration of the amine. Preferably, the introduction of these materials should be such as to result in a substantially complete extraction of lactic acid from the lactate solution with the number of stages utilized. More preferably, the feed ratio of amine phase to lactate solution should be about 40:1 to 1:2 and most preferably about 15:1 to 1:1 by weight.

The trialkyl amine provided to the unit 18 may be introduced in a substantially pure or a diluted form. Because many of the amines applicable to the present process and their salts are relatively viscous, it is preferable to introduce such amines with a solvent. In general, any composition which is miscible with the subject amines and their salts within the range of compositions used and which is reactively inert relative to the system components may be used in the present process. These solvents may be used to control viscosity, enhance extraction or stabilize the organic phase in a manner generally known in the art. Typical examples of solvents which can be used in the present process include liquid hydrocarbons such as kerosene or mineral oil, alkanols such as isopropanol, n-butanol and n-octanol and various ketones such as methyl-isobutyl ketone (MiBK) and nonanone, among others. The extractant used in the process of the present invention may comprise 100% of the trialkyl amine. A more preferred extractant, however, comprises up to about 70% by weight of a solvent or should comprise about 30%–95% by weight of the amine and about 5%–70% by weight of the solvent.

Following extraction within the unit 18, a lactic acid-rich organic phase comprised of lactic acid and the extractant is withdrawn along the path 21 and an aqueous phase or slurry comprised principally of carbonate and/or bicarbonate is withdrawn along the path 20. As used in the description of the preferred embodiment, the term carbonate or bicarbonate refers to the carbonate or bicarbonate salt of the cation of the substance used to neutralize the fermentation. Within the aqueous phase or slurry of the preferred embodiment, the predominant carbonate or bicarbonate is sodium bicarbonate which exists principally as sodium bicarbonate crystals. These are separated from the aqueous raffinate in the solid-liquid separation unit 25. The unit 25 can comprise various filtration, centrifugation or other solid-liquid separation means known in the art. Preferably, however, the sodium bicarbonate crystals are separated by filtration. The aqueous filtrate which in the preferred process is substantially free of lactate may be removed as a component of animal feed or as waste along the path 26. It is also possible, if desired, to recycle all or part of the filtrate back into the system through the streams 11, 14 or 16.

The separated sodium bicarbonate is then directed along the path 29 to a conversion and purification unit 30 for conversion of the sodium bicarbonate to sodium carbonate. Means are known in the art for accomplishing this conversion. In the preferred process, however, the sodium bicarbonate crystals are decomposed in boiling water to produce carbon dioxide and dissolved sodium carbonate. The solution of sodium carbonate is then purified by active carbon treatment and recycled along the path 12 as an alkaline or neutralization component in the fermentation process. The released carbon dioxide can also be reused, if desired. Since the preferred process utilizes sodium carbonate as the neutralizing component in the fermentation process, the aqueous phase after fermentation (stream 14) is comprised of sodium lactate. It is contemplated that other alkali metals, alkaline earth metals or ammonium hydroxides, carbonates or bicarbonates may also be used as the neutralizing agent, in which event the cations in the aqueous phase would be altered accordingly.

The lactic acid-rich organic phase is withdrawn from the unit 18 along the path 21. In the preferred process, the organic phase is decompressed in the flash unit 32 as it leaves the unit 18. This results in the release of a majority of the dissolved carbon dioxide via the stream 33 which may be recycled to streams 19a, 19b or 19c, if desired. This organic phase is made up principally of lactic acid and the extractant. Lactic acid is separated or recovered from this phase in the extraction unit 22, leaving a lactic acid-lean or depleted organic phase which is preferably recycled back to the extraction unit 18 along the path 24 in the form of regenerated extractant. As described above, carbon dioxide may also be added to the recycle stream 24 via the path 19c to load the amine prior to the unit 18. The lactic acid solution is removed from the unit 22 as product via the stream 28.

In the preferred process, the unit 22 is a liquid/liquid extraction unit within which the lactic acid-rich organic phase is back extracted with water introduced along the path 23. Because of the relatively weak amine being used in the primary extraction process and because the amine is water immiscible, the water is able to extract the lactic acid from the amine to form an aqueous solution of lactic acid of acceptable concentration.

In the case where the trialkyl amine is diluted with an appropriate solvent, such solvent becomes a part of the organic phase withdrawn from the unit 18 along the path 21. Some solvents, such as alkanols and ketones, modify and enhance the lactic acid uptake into the organic phase. It is preferable to remove such solvents prior to the back extraction with water in the unit 22. This separation of the solvent from the lactic acid-rich organic phase can be accomplished by various separation techniques known in-the art. Preferably, when possible, the separation is by azeotropic steam distillation within the unit 27. The removed solvent from the separation unit 27 may then be recycled along the path 31 for regeneration of the extractant and use in the primary extraction, if desired.

The lactic acid can also be separated or recovered from the organic phase by vaporization or distillation of the lactic acid. Removal by distillation should preferably be performed at reduced pressure and elevated temperature conditions. Most preferably, the separation should be accomplished at pressures of from about 0.2 to 100 mm Hg and at temperatures from about 80° C. to about 240° C. If this distillation option is employed, the trialkyl amine should have a total of at least 24 carbon atoms, or be sufficiently nonvolatile to allow lactic acid fractionation from the amine by vacuum distillation.

The vaporization conditions will also remove alkanols or ketones, if present, as well as other solvent components more volatile than the trialkyl amine. These can be separately recovered and may be returned to the depleted extractant before it is cycled back to the extraction step. The vapor of lactic acid thus formed may also be directly fed, if desired, to an esterification process for reaction and further purification.

With the above process, lactic acid can be separated and/or removed from a lactate fermentation broth. Under optimal conditions, such separation and/or recovery can approach total recovery of the lactic acid, greater than 95% of that produced by fermentation. Of equal or greater importance is the ability of this recovery to be accomplished with the generation of minimal, if any, waste salt and under circumstances where substantially all of the extraction, conversion and other components used in the process can be recycled for reuse within the process. Still further, the process is significantly less energy intensive than competing processes and results in minimal, if any, plant emissions.

The preferred process has been described with respect to producing lactic acid from a lactate solution formed via a fermentation process. The present process is, however, applicable to the separation and/or recovery of lactic acid from a lactate solution regardless of its origin. For example, polylactide is a biodegradable polymer produced from lactic acid. Polylactide can be recycled by hydrolysis of the polymer to yield a lactate salt. The present process can then be used to recover lactic acid from the lactate salt for reuse in formation of the polylactide polymer.

Further details of the present process are shown and described in the following specific examples.

EXAMPLE 1

A lactate fermentation broth containing 10% by weight of $NaCH_3CH(OH)COO$ (sodium lactate) was withdrawn from a fermentor in which pure carbohydrates were fermented by *Lactobacillus delbrueckii* in the presence of sodium carbonate in order to maintain a pH of 5.5, all as known in the art. The biomass and other solids were removed from the fermentation broth by filtration through ultrafiltration membranes and then concentrated by water evaporation to 50% by weight sodium lactate.

150 g/min of this sodium lactate solution were fed to a 5-stage mixer-settler battery counter-currently to 1050 g/min of regenerated extractant comprising 48% by weight tricaprylylamine (Alamine 336™ produced by Henkel), 20% by weight n-butanol and 32% by weight aromatic-free kerosene. The extraction system was kept at ambient temperature and a 240 psig $CO_2$ atmosphere was maintained therein. Sodium bicarbonate crystals formed in the aqueous phase as of the second mixer-settler.

The aqueous phase was withdrawn and sodium bicarbonate was filtered off from the aqueous raffinate which was practically free of lactate values. The sodium bicarbonate crystals were decomposed in boiling water to $CO_2$ and to dissolved sodium carbonate. This solution was purified by active carbon treatment to a form suitable for use as a base in the fermentation.

The organic phase withdrawn from the last stage of the mixer-settler battery contained 0.65 mole lactic acid per kg. $CO_2$ was allowed to escape from the organic phase, following which the butanol was separated and removed by azeotropic steam distillation. The remaining organic phase was back-extracted with hot water to form a lactic acid-depleted organic phase and an aqueous solution of the lactic acid. The separated butanol was reintroduced into the back-extracted organic phase to regenerate the extractant while the aqueous phase was concentrated and fed to final purification. Removal efficiency of lactic acid from the lactate feed solution was about 95%.

EXAMPLE 2

Aqueous solutions of sodium lactate were equilibrated in a pressure vessel with various extractants under a 220 psig $CO_2$ atmosphere. Contact temperature was 20° C. The initial pH of the aqueous phase and equilibrium data are summarized in the Table below.

TABLE

| Extractant composition | Initial aqueous pH | Equilibrium data | |
|---|---|---|---|
| | | sodium lactate aqueous (wt %) | lactic acid organic (wt %) |
| n-butanol | 5.5 | 62 | 1.05 |
| 80% TDA + 20% i-PrOH | 5.5 | 29.2 | 10.6 |
| 80% TDA + 20% hexane | 5.5 | 39.8 | 2.9 |
| 67% TCA + 33% n-OctOH | 10.9 | 50.3 | 14.3 |
| 70% TCA + 30% n-BuOH | 10.9 | 50.3 | 15.0 |
| 48% TCA + 20% n-BuOH + 32% kerosene | 10.7 | 46.9 | 9.3 |

TDA = tridodecylamine (Henkel)
TCA = tricaprylylamine
i-PrOH = isopropanol
n-OctOH = n-octanol
n-BuOH = n-butanol

EXAMPLE 3

An extractant mixture comprised of 80% by weight tridodecylamine (Alamine 304-1 produced by Henkel) and 20% by weight n-butanol, was contacted with 30% by weight aqueous lactic acid (Purac) in sufficient quantity to produce a loading of 6.9% by weight lactic acid in the organic phase. 230 g of this material was added to a stirred round bottom flask connected to a distillation apparatus, condenser, and controlled vacuum system. The solution was heated to 219° C. at a pressure of 2 mm Hg. Initial condensate fractions included butanol and water. A later fraction showed recovery of 97% by weight of the original lactic acid. The residual extractant contained 0.2% by weight lactic acid. The composition of the pooled fractions containing the acid was 98.3% by weight aqueous lactic acid and 1.7% by weight of its oligomers. The depleted extractant was replenished with butanol and cycled back for another extraction. Five such cycles were run on one batch without significant loss of extractant performance.

EXAMPLE 4

Various experiments were conducted in a Parr pressure reactor for the purpose of showing the applicability of the process of the present invention to a broad range of $CO_2$ pressures, to a variety of solvents and to representative samples of trialkyl water immiscible amines with a total carbon content of at least 18.

The apparatus comprised a Parr pressure reactor with four agitators, gas inlet and outlet ports, aqueous and organic sample ports and a pressure gage. The procedure involved adding the aqueous and the pre-mixed organic solutions to the Parr reactor. Except for Experiment Nos. 7, 12, 18 and 21 below in which the ratio of organic to aqueous was 1:3, the ratio of organic to aqueous in all experiments was 1:1. The aqueous solution was comprised of sodium lactate (NaLa), calcium lactate (CaLa) or potassium lactate (KLa). The NaLa solutions comprised about 20%–40% by weight of the lactate, the KLa solution comprised about 20% by weight of the lactate, while the CaLa solution comprised about 6% by weight of the lactate. Further, in Experiment Nos. 7–10, 12–18 and 20–24, 10% by weight sodium bicarbonate was added for the purpose of saturating the solution. The organic solution comprised a trialkyl amine or a mixture of a trialkyl amine and one or more solvents.

The Parr pressure reactor was then assembled and a slow flow of $CO_2$ was introduced for about 5 minutes to purge the air in the reactor. The $CO_2$ pressure was then adjusted to the desired level. It should be noted that the pressures identified in the table below are gage pressures. Thus, a $CO_2$ level of 0 psig as indicated in Experiment Nos. 1 and 13 reflect a $CO_2$ partial pressure of 14.7 psi. The $CO_2$ pressure was maintained at the selected level, with a slow bleed of $CO_2$ (about 100 ml/min) bubbling through the contents, and the contents in the reactor were agitated for two hours. The $CO_2$ inlet and outlet ports were then sealed and agitation continued for 10 more minutes, at which time agitation was terminated and the contents were allowed to settle for 30 minutes. Samples of both the organic and aqueous phases were collected through the organic and aqueous sample ports, after which the above procedure repeated for a different $CO_2$ pressure. All experiments were run at 25° C.

All organic samples were analyzed with NaOH to a phenolphthalein endpoint to determine concentration of lactic acid in the organic phase. All aqueous samples were analyzed by HPLC to determine lactic acid equivalent in the aqueous phase. The partition coefficient (K) was then calculated by dividing the concentration of lactic acid in the organic phase by the concentration of lactate, expressed as lactic acid equivalent, in the aqueous phase.

The table below reflects data from selected experiments conducted in accordance with the above procedure in which the amines and solvents are identified as follows. All percentages are by weight unless otherwise specified.

| Amines | Solvents |
|---|---|
| A1 = trihexylamine | CS1 = n-octanol |
| A2 = trioctylamine | CS2 = n-butanol |
| A3 = triisooctylamine | CS3 = nonenone |
| A4 = tricaprylylamine | CS4 = Isopar K, Exxon |
| A5 = tridodecylamine | |

| No. | Organic | Aqueous | $CO_2$ Press. (psig) | K C(org)/C(aq.) | Final Aq. Wt % Lac. |
|---|---|---|---|---|---|
| 1 | A4(48%), CS1(30%), CS4(22%) | CaLa | 0 | 0.068 | 2.21 |
| 2 | A4(48%), CS1(30%), CS4(22%) | CaLa | 150 | 0.388 | 2.06 |
| 3 | A4(48%), CS1(30%), CS4(22%) | CaLa | 220 | 0.553 | 1.99 |
| 4 | A4(48%), CS1(30%), CS4(22%) | CaLa | 300 | 0.622 | 1.93 |
| 5 | A4(48%), CS1(30%), CS4(22%) | KLa | 75 | 0.112 | 18.8 |
| 6 | A4(48%), CS1(30%), CS4(22%) | KLa | 500 | 0.198 | 17.5 |
| 7 | A4(48%), CS1(30%), CS4(22%) | NaLa (sat) | 75 | 0.047 | 19.9 |
| 8 | A4(48%), CS1(40%), CS4(12%) | NaLa (sat) | 150 | 0.093 | 38.3 |
| 9 | A4(48%), CS1(40%), CS4(12%) | NaLa (sat) | 200 | 0.155 | 38.0 |
| 10 | A4(48%), CS1(40%), CS4(12%) | NaLa (sat) | 300 | 0.199 | 37.5 |
| 11 | A4(48%), CS2(35%), CS4(17%) | NaLa | 220 | 0.255 | 29.8 |
| 12 | A1(33%), CS1(30%), CS4(37%) | NaLa (sat) | 240 | 0.123 | 20.1 |
| 13 | A2(43%), CS1(30%), CS4(27%) | NaLa (sat) | 0 | 0.038 | 21.9 |
| 14 | A2(43%), CS1(30%), CS4(27%) | NaLa (sat) | 75 | 0.064 | 21.6 |
| 15 | A2(43%), CS1(30%), CS4(27%) | NaLa (sat) | 240 | 0.119 | 20.7 |
| 16 | A4(48%), CS3(52%) | NaLa (sat) | 240 | 0.069 | 21.6 |
| 17 | A3(43%), CS1(30%), CS4(27%) | NaLa (sat) | 75 | 0.038 | 20.3 |
| 18 | A3(43%), CS1(30%), CS4(27%) | NaLa (sat) | 240 | 0.097 | 20.0 |
| 19 | A5(48%), CS2(20%), CS4(32%) | NaLa | 220 | 0.266 | 34.4 |
| 20 | A4(100%) | NaLa (sat) | 75 | 0.020 | 21.4 |
| 21 | A4(100%) | NaLa (sat) | 240 | 0.047 | 21.4 |
| 22 | A4(43%), CS1(30%), CS4(27%) | NaLa (sat) | 500 | 0.208 | 19.8 |
| 23 | A4(48%), CS3(52%) | NaLa (sat) | 500 | 0.102 | 21.3 |

| 24 | A4(48%), CS4(52%) | NaLa (sat) | 500 | 0.020 | 21.8 |

We claim:

1. A process for the recovery of lactic acid from a lactate feed solution comprising:

the extraction step of combining said lactate feed solution with an extractant comprising at least one water immiscible trialkyl amine having a total of at least 18 carbon atoms in the presence of carbon dioxide at a partial pressure of at least 50 psig to form an aqueous phase and an organic phase containing extracted lactic acid and said extractant and separating lactic acid from said organic phase.

2. The process of claim 1 including separating lactic acid from said organic phase by extraction with water.

3. The process of claim 1 including separating lactic acid from said organic phase by vaporization of lactic acid.

4. The process of claim 3 wherein said vaporization is carried out under vacuum at an absolute pressure of from 0.2 to 100 mm Hg and a temperature of from 80° C. to 240° C.

5. The process of claim 1 including separating lactic acid from said organic phase, leaving a lactic acid-lean organic phase.

6. The process of claim 5 further comprising recycling at least a portion of said lactic acid-lean organic phase for use in said extraction step.

7. The process of claim 1 wherein said extractant includes at least one solvent compatible with and substantially chemically inert relative to lactic acid and said at least one water immiscible trialkyl amine.

8. The process of claim 7 wherein said solvent is selected from the group comprising hydrocarbons, alkanols, ketones and mixtures thereof.

9. The process of claim 8 wherein said solvent is selected from the group comprising alkanols and ketones capable of forming an azeotrope with water.

10. The process of claim 7 further comprising first removing at least a portion of said solvent and secondly removing lactic acid contained in said organic phase, and then recycling at least a portion of the remaining organic phase for use in said extraction step.

11. The process of claim 10 wherein said solvent is selected from the group of alkanols and ketones capable of forming an azeotrope with water and said process includes removing said alkanols and ketones by azeotropic steam distillation.

12. The process of claim 1 where the total number of carbon atoms of said at least one water immiscible trialkyl amine is from 24 to 42.

13. The process of claim 1 wherein said one water immiscible trialkyl amine is selected from the group of trihexylamine, trioctylamine, triisooctylamine tricaprylylamine, tridodecylamine and mixtures thereof.

14. A process of producing lactic acid comprising:

obtaining a lactate feed solution from a fermentation process and recovering lactic acid from said lactate feed solution in accordance with the process of claim 1.

15. The process of claim 14 including maintaining the pH of said fermentation process at a pH greater than 4.5 by addition of a neutralizing agent.

16. The process of claim 15 wherein said neutralizing agent includes at least one of an alkali metal, alkaline earth metal or ammonium as the cation and at least one of hydroxide, carbonate or bicarbonate as the anion.

17. The process of claim 16 wherein the combining of the lactate feed solution and said extractant results in the formation of an organic phase containing lactic acid and said extractant and an aqueous phase containing carbonate or bicarbonate salt.

18. The process of claim 17 wherein said aqueous phase contains carbonate or bicarbonate in a solid form which has been precipitated from the aqueous phase.

19. The process of claim 18 including separating said carbonate or bicarbonate salt from said aqueous phase, leaving an aqueous raffinate.

20. The process of claim 17 including recycling at least a portion of said carbonate; or bicarbonate salt for use in said fermentation process.

21. The process of claim 20 wherein a fermentation broth is obtained by fermentation of the bacterial genus lactobacillus during said fermentation process.

22. The process of claim 15 wherein a fermentation broth is formed in a fermentor during said fermentation process and said process further includes forming said lactate feed solution by filtering the fermentation broth to remove biomass and other solids.

23. The process of claim 22 wherein said lactate feed solution is concentrated by water removal to 40% to 70% by weight sodium lactate.

24. The process of claim 1 being a continuous process.

25. The process of claim 1 wherein the combining of said lactate feed solution and said extractant is carried out in a multi-stage, counter-current liquid/liquid extractor.

26. The process of claim 1 wherein at least 95% by weight of said lactate is recovered as lactic acid.

27. The process of claim 1 wherein said extractant and said lactate feed solution are continuously combined and the feed ratio by weight of extractant to lactate feed solution is 40:1 to 2:1.

28. The process of claim 1 wherein said lactate feed solution is formed by the hydrolysis of polylactide.

29. A process for recovering lactic acid from an aqueous lactate solution at a pH of at least 4.5 comprising:

combining said lactate solution with an extractant comprised of at least one trialkyl amine having at least 18 carbon atoms in the presence of carbon dioxide at a partial pressure of at least 50 psig to form an aqueous phase and an organic phase containing extracted lactic acid and said extractant and separating lactic acid from said organic phase.

30. A continuous process for producing lactic acid comprising:

producing lactic acid by a fermentation process to form a fermentation broth;

maintaining said fermentation broth at a desired pH by addition of a neutralizing agent comprised of at least one of an alkali metal, alkaline earth metal or ammonium as the cation and at least one of hydroxide, carbonate or bicarbonate as the anion whereby the lactic acid in said fermentation broth is converted to a salt form comprising the lactate anion;

removing a portion of said fermentation broth as a lactate feed solution;

performing an extraction step by combining said lactate feed solution and an extractant comprised of at least one water immiscible trialkyl amine in the presence of carbon dioxide at a partial pressure of at least 50 psig to form an organic phase containing extracted lactic acid and said extractant and an aqueous phase containing carbonate or bicarbonate salts;

separating lactic acid from said organic phase leaving a lactic acid-lean organic phase;

recycling at least a portion of said lactic acid-lean organic phase for use in said extraction step; and recycling at least a portion of said carbonate or bicarbonate salts for use in said fermentation process as said neutralizing agent.

* * * * *